United States Patent

Tang et al.

Patent Number: 5,998,670
Date of Patent: Dec. 7, 1999

[54] METHOD OF MAKING HIGH PURITY SUBSTITUTED DIPHENYLDISULFIDES

[75] Inventors: David Y. Tang, East Amherst; Michael C. Hausladen, Amherst; Viktor D. Sorokin, Grand Island, all of N.Y.

[73] Assignee: Occidental Chemical Corporation, Dallas, Tex.

[21] Appl. No.: 09/040,612

[22] Filed: Mar. 18, 1998

[51] Int. Cl.[6] .................................................. C07C 321/00
[52] U.S. Cl. ................................ 568/26; 568/23; 568/24; 568/25
[58] Field of Search ................................ 568/21, 23, 24, 568/25, 26

[56] References Cited

U.S. PATENT DOCUMENTS 2,181,037  11/1939  Wilson .
5,659,086  8/1997  Pauwels ..................................... 568/26

OTHER PUBLICATIONS

M. E. Niyazymbetov et al., "Electrooxidation of Thiols in the Presence of Halide Ions —A Facile Preparative Method for Synthesis of Disulfides", Synthetic Communications, 23(12), 1659–1665 (1993).

H. M. Meshram, "Improved and Convenient Synthesis of Disulfides In The Absence of Solvent Catalyzed By Clayfen", OPPI Briefs, vol. 25, No. 2 (1993) pp. 232–233.

X. Wu et al., "Preparation of Disulfides By The Oxidation Of Thiols Using Bromine", Synthetic Communications, 26(1), 191–196 (1996).

A. McKillop et al., "Efficient, High Yield Oxidation of Thiols and Selenols to Disulphides and Diselenides", Tetrahedron Letters, vol. 31, No. 35, pp. 5007–5010 (1990).

J. Drabowicz et al., "A Simple Procedure for the Oxidation of Thiols To Disulphides By Means of Bromine/Aqueous Potassium Hydrogen Carbonate In A Two–Phase System", Synthesis, pp. 32–34, (Jan. 1980).

K. Ramadas et al., "Sodium Chlorite —Yet Another Oxidant For Thiols To Disulphides", Synthetic Communications, 25(2), 227–234 (1995).

K–T Liui et al., "A Facile Conversation of Thiols To Disulfides", Synthesis, pp. 669–670 (1978).

Ogawa et al., "Benzotrifluoride . . . " J. Org. Chem. 1997, 62, 450–451.

Gilbert, J Am Chem Soc 102 vol. 23, pp. 7059–7065, 1980.

Kice, J Am Chem Soc 98 vol. 24, pp. 711–7716, 1976.

*Primary Examiner*—Gary Geist
*Assistant Examiner*—Jean F Vollano
*Attorney, Agent, or Firm*—Anne E. Brookes; Richard D. Fuerle

[57] ABSTRACT

Disclosed is a method of making a substituted diphenyldisulfide from a substituted thiophenol. A two phase reaction mixture is prepared which comprises a substituted thiophenol having the general formula

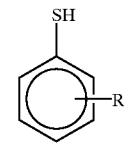

hydrogen peroxide, water, an organic solvent, a basic salt that will give a pH between about 7 and about 10, and an optional flocculating agent. In the formula, R is selected from the group consisting of halogen, alkyl from $C_1$ to $C_6$, alkoxy from $C_1$ to $C_6$, or nitro. After the exothermic reaction is complete, the reaction mixture is cooled to crystallize the substituted diphenyldisulfide product. The symmetrical product precipitates preferentially over the unsymmetrical product, thereby enhancing the purity of the product over the purity of the starting material. Optionally, the organic solvent and the aqueous phase are recycled.

20 Claims, No Drawings

METHOD OF MAKING HIGH PURITY SUBSTITUTED DIPHENYLDISULFIDES

BACKGROUND OF THE INVENTION

This invention relates to a method of making a high purity substituted diphenyldisulfide by reacting a substituted thiophenol with hydrogen peroxide in the presence of a catalytic amount of a basic salt. In particular, this invention relates to performing the reaction in a two phase water-organic solvent system where the symmetrical product is less soluble in the organic solvent than the unsymmetrical product, and therefore the purity of the product is greater than the purity of the thiophenol starting material.

High purity 4,4'-dichlorodiphenyldisulfide is used to make various pharmaceuticals such as bisphosphonates. It can be made by oxidizing parachlorothiophenol with an oxidizing agent, such as bromine, but this route is expensive and results in the production of large amounts of waste hydrogen bromide. Hydrogen peroxide can also be used to make this product from parachlorothiophenol, but, because the starting material also includes some orthochlorothiophenol, the product contains both the symmetrical 4,4'-dichlorodiphenyldisulfide isomer and the unsymmetrical 2,4'-dichlorodiphenyldisulfide. The presence of small quantities of the 2,4'-dichlorodiphenylsulfide in the product is not acceptable for the production of pharmaceuticals.

SUMMARY OF THE INVENTION

We have discovered that if substituted diphenyldisulfides are made by oxidizing a thiophenol with hydrogen peroxide in a two phase system consisting of water and an organic solvent, the symmetrical product is less soluble in the organic solvent than the unsymmetrical product. Thus, if the starting material is impure, as it invariably is, the purity of the product is enhanced by the process of this invention.

The process of this invention uses relatively inexpensive materials and produces only water as the principle waste product. A major advantage of this invention is that the organic solvent and the aqueous phase can be recycled.

DESCRIPTION OF THE PREFERRED EMBODIMENTS

In the process of this invention, a substituted diphenyldisulfide is produced from a substituted thiophenol starting material which has the general formula:

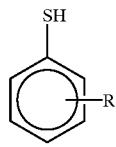

where R is halogen, alkyl from $C_1$ to $C_6$, alkoxy from $C_1$ to $C_6$, or nitro. The R group is preferably chlorine or fluorine as those compounds are commercially more important. A para substituted R group is also preferred for the same reason. While the invention can be used with 100% pure substituted thiophenol, it is more applicable to substituted thiophenols that are somewhat impure in that they contain small amounts of other position isomers because the invention results in an enhancement in the purity of the product when those less pure starting materials are used. Preferably, the substituted thiophenol contains about 0.3 to about 3 wt % of isomers other than the principal isomer.

In the process of this invention, the reaction is performed in a two phase system. One phase is water containing hydrogen peroxide and a catalytic amount of a basic salt and the second phase is an organic solvent. The proportion of water to organic solvent can vary over a large range. Sufficient water should be used so that the reaction mixture can be processed easily, but excess water is unnecessary. The amount of water is preferably about 10 to about 200 volume % of the volume of the organic solvent.

The amount of hydrogen peroxide is generally about stoichiometric with the amount of substituted thiophenol but up to about 1 wt % excess is advisable to make up for losses.

Any salt, organic or inorganic, that will give a pH between about 7 and about 10, and preferably between about 8 and 9, can be used in the process of this invention. The purpose is of the basic salt is to react with the hydrogen peroxide to form the peroxy anion, HOO—, and an aryl sulfide anion. Higher pH's are undesirable because hydrogen peroxide decomposes faster at higher pH's and selectivity is reduced (i.e., the production of over-oxidized unwanted byproducts increases). Also, a strong base can break the disulfide bond, reducing the yield of the product. Examples of suitable bases include sodium carbonate, potassium carbonate, calcium hydroxide, tetraalkyl aluminum hydroxides, such as tetramethyl ammonium hydroxide or tetraethyl ammonium hydroxide, and alkali metal salts of borates, such as sodium borate or potassium borate. Sodium carbonate is preferred because it is inexpensive and has been found to work well. Sufficient basic salt should be used to produce the desired pH. Typically, about 0.1 to about 5 wt %, based on the weight of the aqueous phase, is sufficient and preferably about 1 to about 2 wt % is used.

Any organic solvent can be used to form the organic phase, provided that it is inert and does not react with the hydrogen peroxide. The organic solvent should be a liquid and should preferably boil at a temperature higher than the maximum reaction temperature. Examples of suitable organic solvents include methylene chloride, perchloroethylene, chlorobenzene, and benzotrifluoride. The preferred organic solvent is benzotrifluoride (BTF) because both the symmetrical and the unsymmetrical reaction products are very soluble in it at the reaction temperature and less soluble at room temperature, so that most of the reaction products precipitate upon cooling.

An optional flocculating agent can also be added to the mixture to prevent the formation of an emulsion between the water and the organic phase. Almost any highly ionic compound or strong electrolyte will function as a flocculating agent in this reaction such as, for example, sodium chloride or potassium chloride; sodium chloride is preferred as it is inexpensive. The amount of flocculating agent used is preferably about 1 to about 2 wt %, based on the weight of the water phase.

The components of the reaction mixture can be added together in almost any order but it is advisable to add the hydrogen peroxide last, slowly, and with vigorous stirring as it induces an exothermic reaction and selectivity may be lost if the reaction is too rapid. Since the reaction is exothermic, it is not necessary to heat the reaction mixture. It is preferable to keep the temperature of the reaction mixture below about 80° C., and preferably below about 50° C., because at higher temperatures selectivity may be lost. Vigorous stirring and agitation of the reaction mixture is advisable to ensure a complete reaction. Upon completion of the reaction, the reaction mixture is cooled to room temperature or to a lower temperature, which results in the precipitation of the product. The symmetrical product is typically about 3 to about 5 times less soluble in the organic phase than is the unsymmetrical product and will preferentially crystallize, enhancing the purity of the product over the purity of the starting material, the substituted thiophenol. The precipitated product can then be collected by filtration and dried. The product has the formula:

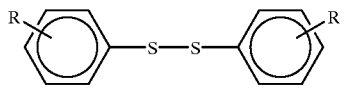

Preferably, the organic solvent and aqueous phase are recycled.

The following example further illustrates this invention.

EXAMPLE 1

Into a 1 liter three-necked round bottom flask fitted with a condenser, 60 mL addition funnel, and agitator was charged 150 g of 4-chlorothiophenol (containing 0.3 wt % 2-chlorothiophenol), 300 mL of BTF, 300 mL of water and 7.5 g sodium carbonate, while into the addition funnel was charged 60 mL of 30 wt % hydrogen peroxide solution. The agitation was started and the hydrogen peroxide added dropwise over a period of 3.5 hours. The reaction mixture was heated to 45° C. and transferred to a separatory funnel. The organic layer was separated and placed into an agitated 500 mL Erlenmeyer flask. The organic layer was cooled to room temperature and the crystallized solid 4,4'-dichlorodiphenyldisulfide was filtered and dried. 111 g of 4,4'-dichlorodiphenyldisulfide was collected. Purity by gas chromatography (GC) showed no detectable isomer impurities.

This example was repeated, except that the crystallization was performed in the flask. Similar results were obtained.

EXAMPLE 2

Using the same equipment as in Example 1, 152 g of 4-chlorothiophenol (containing 0.3% 2-chlorothiophenol), 300 mL of BTF and 300 mL of the aqueous layer from Example 1 were charged into the 1 L flask, while into the addition funnel was charged 60 mL of 30 wt % hydrogen peroxide solution. The reaction, phase separation, filtration, and drying were done as in Example 4 and 114 g of dry 4,4-dichlorodiphenyldisulfide were collected. Purity by GC showed no detectable isomer impurities.

EXAMPLE 3

Using the same equipment as in Example 1, 152 g of 4-chlorothiophenol (containing 0.3% 2-chlorothiophenol), 250 mL of the organic layer from Example 2, 50 mL of BTF, and 300 mL of the aqueous layer from Example 1 were charged into the 1 L flask, while into the addition funnel was charged 60 mL of 30 wt % hydrogen peroxide solution. The reaction, phase separation, filtration, and drying were done as in Example 4 and 127 g of dry 4,4-dichlorodiphenyldisulfide was collected. Purity by GC showed no detectable isomer impurities.

EXAMPLE 4

Into a three-necked, round-bottom flask equipped with an addition funnel, nitrogen inlet, thermocouple, heating mantle, and magnetic stirrer, was placed 15.02 g (121 mmol) of p-thiocresol, 35 mL BTF, 15 mL water, and 0.97 g (9 mmol) sodium carbonate. To the mixture was gradually (over 20 to 30 minutes) added with stirring 8.07 g of 35 wt % hydrogen peroxide and the temperature was established at 50° C. After 30 minutes of stirring at this temperature, the mixture was cooled down and the organic layer was separated and dried with sodium sulfate. The BTF was removed under reduced pressure (water aspirator) and 13.86 g (93% yield) of a yellow oil (p-tolyl disulfide) was obtained. The oil was slowly crystallized at room temperature to give a white-yellow solid with a mp of 44–45° C. (An Aldrich sample of p-tolyl disulfide had a mp of 43–46° C.) The purity according to GC was 99%.

EXAMPLE 5

Into a three-necked, round bottom flask equipped with an addition funnel, $N_2$ inlet tube, thermocouple, heating mantle, and magnetic stirrer was placed 7.5 g (52 mmol) p-chlorothiophenol, 25 mL tetrachloroethylene, 20 mL water, and 0.45 g (4.25 mmol) sodium carbonate. To the mixture at room temperature was gradually (for 20 (–30 min) added with stirring 3.5 mL (30.9 mmol) of 35 wt % hydrogen peroxide. After an hour of stirring at room temperature, the organic layer (bottom) was separated and dried with magnesium sulfate. The tetrachloroethylene was removed under reduced pressure (water aspirator) and 6.95 g (93% yield) of a yellow solid with mp 71–72° C. (literature mp=67.5–69.5, 70–71, and 73° C.) was recovered. The purity of the product (according to GC) was over 99%.

EXAMPLE 6

Into a three-necked, round bottom flask equipped with an addition funnel, $N_2$ inlet tube, thermocouple, heating mantle, and magnetic stirrer was placed 198.5 g (1.37 mol) p-chlorothiophenol, 110 mL monochlorobenzene, 160 mL water, 12 g (0.113 mol) sodium carbonate, and 4.05 g (0.069 mol) sodium chloride. To the mixture was gradually (for 1 hour) added with stirring 86.0 g (0.885 mol) of 35 wt % hydrogen peroxide and the temperature was established at 50° C. After 30 minutes of stirring at this temperature, the mixture was cooled to 10° C. A yellow solid precipitated and the reaction mixture looked like a thick suspension. Solids were separated by filtration and 196.48 g of wet product was obtained. The solids were washed with water (300 ml) and dried under vacuum for 15 hours at 50° C. After drying, 151.2 g (77%) of the product with the purity over 99% and mp 71–72° C. was obtained. The mother liquor contained an additional amount of disulfide (about 40 g) which could be isolated by evaporating the solvent. The total yield was close to quantitative.

We claim:

1. A method of making a symmetrical substituted diphenyldisulfide containing a reduced amount of unsymmetrical substituted diphenyldisulfides comprising (A) adding together components which comprise (1) a substituted thiophenol having the general formula

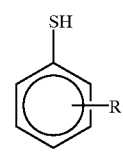

where R is selected from the group consisting of halogen, alkyl from $C_1$ to $C_6$, alkoxy from $C_1$ to $C_6$, and nitro, where said substituted thiophenol contains a small amount of position isomers other than the principal isomer,
(2) hydrogen peroxide;
(3) an inert organic solvent that will not react with said hydrogen peroxide and that will form a two phase reaction mixture with water;
(4) water;
(5) a basic salt that produces a pH in said water between about 7 and about 10; and
(6) up to about 2 wt %, based on the weight of said water, of a flocculating agent, whereby a two phase reaction mixture is formed;

(B) allowing the temperature of said reaction mixture to rise to a temperature up to about 80° C.; and (C) cooling said reaction mixture to a temperature of room temperature or lower, whereby said symmetrical substituted diphenyldisulfide preferentially crystallizes.

2. A method according to claim 1 wherein R is chlorine.

3. A method according to claim 1 wherein R is fluorine.

4. A method according to claim 1 wherein said reaction mixture is stirred vigorously and said hydrogen peroxide is added slowly and last.

5. A method according to claim 1 wherein said substituted thiophenol is 97 to 99.7 wt % of one position isomer and 0.3 to 3 wt % of other position isomers.

6. A method according to claim 5 wherein about 97 to about 99.7 wt % of said substituted thiophenol is para substituted.

7. A method according to claim 1 wherein the amount of water is about 10 to about 200 vol % of the volume of said organic solvent.

8. A method according to claim 1 wherein said basic salt produces a pH in said water between about 8 and about 9.

9. A method according to claim 1 wherein said basic salt is sodium carbonate.

10. A method according to claim 1 wherein said inert organic solvent is benzotrifluoride.

11. A method according to claim 1 wherein said inert organic solvent and said water are recycled to step (A).

12. A method of making a 4,4'-substituted diphenyldisulfide containing a reduced amount of other position isomers comprising (A) vigorously stirring a two phase reaction mixture which comprises
(1) a substituted thiophenol having the general formula

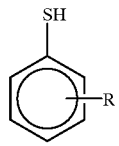

where R is in the para position and is selected from the group consisting of chlorine and fluorine, where said substituted thiophenol contains a small amount of position isomers other than the principal isomer;
(2) an organic solvent selected from the group consisting of methylene chloride, perchloroethylene, chlorobenzene, and benzotrifluoride;
(3) water in an amount of about 10 to about 200 vol % of the volume of said organic solvent;
(4) a basic salt that produces a pH in said water between about 7 and about 10; and
(5) up to about 2 wt % based on the weight of said water of a flocculating agent, (B) adding hydrogen peroxide to said two phase reaction mixture;

(C) allowing the temperature of said reaction mixture to rise to a temperature up to about 80° C.; and (D) cooling said reaction mixture to a temperature of room temperature or lower, whereby said 4,4'-substituted diphenyldisulfide precipitates.

13. A method according to claim 12 wherein the amount of said hydrogen peroxide added is about stoichiometric.

14. A method according to claim 12 wherein said basic salt produces a pH in said water between about 8 and about 9.

15. A method according to claim 12 wherein said basic salt is sodium carbonate.

16. A method according to claim 12 wherein said inert organic solvent is benzotrifluoride.

17. A method according to claim 12 wherein said inert organic solvent and said water are recycled to step (A).

18. A method of making 4,4'-dichlorodiphenyldisulfide containing a reduced amount of other position isomers comprising (A) forming a two phase reaction mixture which comprises
(1) 4-chlorothiophenol containing about 0.3 to about 3 wt % of other position isomers;
(2) hydrogen peroxide;
(3) an organic solvent selected from the group consisting of chlorobenzene or benzotrifluoride;
(4) water in an amount of about 10 to about 200 vol % of the volume of said organic solvent;
(5) about 0.1 to about 5 wt %, based on the weight of said water, of a basic salt that produces a pH in said water between about 8 and about 9; and
(6) up to about 2 wt %, based on the weight of said water, of a flocculating agent;

(B) allowing the temperature of said reaction mixture to rise to a temperature up to about 50° C.;

(C) cooling said reaction mixture to a temperature of room temperature or lower, whereby said 4,4'-dichlorodiphenyldisulfide precipitates; and (D) recycling said inert organic solvent and said water to step (A).

19. A method according to claim 18 wherein said 4-chlorothiophenol contains about 0.3 to about 3 wt % 2-chlorothiophenol.

20. A method according to claim 18 where said 4,4'-dichlorodiphenyldisulfide is collected by filtration and dried.

* * * * *